(12) United States Patent
Konno (10) Patent No.: US 8,926,678 B2
(45) Date of Patent: Jan. 6, 2015

(54) HANDPIECE FOR LASER TREATMENT DEVICE

(75) Inventor: Akira Konno, Yamanashi-ken (JP)

(73) Assignee: Altech Corporation, Yamanashi-Ken (JP)

(*) Notice: Subject to any disclaimer, the term of this patent is extended or adjusted under 35 U.S.C. 154(b) by 0 days.

(21) Appl. No.: 14/009,956

(22) PCT Filed: Apr. 2, 2012

(86) PCT No.: PCT/JP2012/058818
§ 371 (c)(1),
(2), (4) Date: Feb. 19, 2014

(87) PCT Pub. No.: WO2012/137700
PCT Pub. Date: Oct. 11, 2012

(65) Prior Publication Data
US 2014/0180368 A1 Jun. 26, 2014

(30) Foreign Application Priority Data
Apr. 7, 2011 (JP) ............... PCT/JP2011/058819

(51) Int. Cl.
*A61N 5/06* (2006.01)
*A61B 18/18* (2006.01)
*A61B 18/22* (2006.01)

(52) U.S. Cl.
CPC ............ *A61N 5/0625* (2013.01); *A61B 18/22* (2013.01); *A61B 2018/2211* (2013.01); *A61B 2018/225* (2013.01); *A61B 2018/2255* (2013.01)
USPC ............................................. 607/89; 606/16

(58) Field of Classification Search
CPC ..... A61N 5/06; A61N 5/0616; A61N 5/0625; A61N 2005/0626; A61N 2005/0627; A61N 2005/063; A61N 2005/0644; A61B 18/22; A61B 2018/225; A61B 2018/2255; A61B 2018/209; A61B 2018/2085
USPC ............................. 606/9, 16; 607/88, 89, 100
See application file for complete search history.

(56) References Cited

U.S. PATENT DOCUMENTS

| 4,491,385 A | * | 1/1985 | Imagawa et al. | ............... 385/139 |
| 5,346,489 A | * | 9/1994 | Levy et al. | ...................... 606/15 |

(Continued)

FOREIGN PATENT DOCUMENTS

| JP | 2000023998 | 1/2000 |
| JP | 2001502438 | 2/2001 |

(Continued)

OTHER PUBLICATIONS

Search Report issued on Feb. 6, 2014 related to corresponding European Patent Application No. 12767872.0.

(Continued)

*Primary Examiner* — Lynsey Crandall
*Assistant Examiner* — Nathan J Jenness
(74) *Attorney, Agent, or Firm* — Onello & Mello, LLP (57) ABSTRACT

Provided is a handpiece of a laser treatment device which can restrict a temperature rise of body tissues in a path from an irradiation portion to a target region more effectively than in the related art. The handpiece 10 includes an optical fiber 16 which guides laser light emitted from a pulse light source, and a revolving holder which holds a tip portion 64 of the optical fiber 16 such that the tip portion 64 is tilted with respect to a rotational axis C0 to direct an optical axis C1 of the laser light towards a target point P located on the rotational axis C0 and revolves the tip portion 64 of the optical fiber 16 about the rotational axis C0. Further, a pulse number of the pulse light source per unit time and a number of revolutions of the tip portion 64 of the optical fiber 16 per unit time are determined such that the pulse number of the pulse light source per unit time is not an integral multiple of the number of rotations of the tip portion 64 of the optical fiber 16 per unit time.

2 Claims, 9 Drawing Sheets

(56) References Cited

U.S. PATENT DOCUMENTS

| | | | |
|---|---|---|---|
| 5,628,744 A * | 5/1997 | Coleman et al. | 606/12 |
| 5,851,112 A * | 12/1998 | Daikuzono et al. | 433/29 |
| 6,004,315 A | 12/1999 | Dumont | |
| 2001/0007078 A1 | 7/2001 | Yayama | |
| 2007/0038274 A1 | 2/2007 | Ishii et al. | |
| 2009/0043247 A1 | 2/2009 | Kreindel et al. | |
| 2011/0270364 A1 | 11/2011 | Kreindel et al. | |

FOREIGN PATENT DOCUMENTS

| | | |
|---|---|---|
| JP | 2001187157 | 7/2001 |
| JP | 2003079752 | 3/2003 |
| JP | 2003117008 | 4/2003 |
| JP | 2003265498 | 9/2003 |
| JP | 2004329473 | 11/2004 |
| JP | 2004329475 | 11/2004 |
| JP | 2010535056 | 11/2010 |
| KR | 101016694 | 2/2011 |

OTHER PUBLICATIONS

Takahashi, et al.. "A Study on Intracutaneous Temperature Measurements During the Emission of Skin Tightening Devices", pp. 53-60.

Key, "Single-Treatment Skin Tightening by Radiofrequency and Long-Pulsed, 1064-nm Nd: YAG Laser Compared", 2007 Wiley-Liss, Inc.

* cited by examiner

HANDPIECE FOR LASER TREATMENT DEVICE

TECHNICAL FIELD

The present invention relates to a handpiece for a laser treatment device, and more particularly to a handpiece used for a laser treatment device that irradiates body tissues with laser light to warm them in order to treat the body tissues.

BACKGROUND ART

Treatment devices of electromagnetic wave irradiation type which treat tissues by irradiating body tissues such as the skin with electromagnetic waves to treat the tissues have been conventionally known. For example, Patent Document 1 and Non-patent Document 1 disclose treatment devices which irradiate skin with RF waves. In these treatment devices, with radiation of RF waves onto the skin, regeneration of epidermis is stimulated by warming the skin, or regeneration and growth of collagen are stimulated by warming the dermis.

A treatment device of electromagnetic wave irradiation type is structured to include a power supply device provided with an electromagnetic wave source and a power supply; and a treatment tool called a handpiece connected to the power supply device. The handpiece is provided with an irradiation unit which radiates electromagnetic waves to a treatment target such as the skin. For example, when RF waves are used as electromagnetic waves, a pair of electrodes is mounted on the irradiation unit. After the pair of electrodes is brought into contact with the skin, electromagnetic waves such as RF waves are transmitted from the electrodes. The electromagnetic waves emitted from one of the pair of the electrodes reach the other electrode via the skin. Skin tissues in the path of transmission of the electromagnetic waves in this process are warmed.

In this occasion, even if a target region is smaller than a region which is covered by the flow path of the electromagnetic waves, basically, the whole path is warmed equally with the target region. It should be noted that a patient may feel pain by the temperature rise of body tissues. Although such a pain is endurable without anesthesia, there is a demand to reduce the size of the region causing the pain in consideration of the burden of the patient. Thus, in Patent Document 1, a cooler is mounted on a handpiece to restrict the temperature rise of the tissues outside the target region by bringing the cooler in contact with the skin surface.

PRIOR ART DOCUMENT

Patent Documents

Patent Document 1: JP 2010-535056A

Non-Patent Documents

Non-Patent Document 1: Takahashi, "Measurement and Study of Intradermal Temperature Change by Various Kinds of Skin Tightening Devices", Journal of the Japanese Society for Aesthetico-Medical Technology, Japanese Society for Aesthetico-Medical Technology, Jun. 30, 1998, No. 3, pp. 53-60

DISCLOSURE OF THE INVENTION

Objects to be Achieved by the Invention

With the structure for bringing the cooler in contact with the skin surface, although it is possible to achieve a cooling effect on the skin surface, the cooling effect is limited because tissues under skin surface, such as dermis tissues, outside the target region in the path of electromagnetic waves are warmed almost to the same extent as those in the target region. Thus, treatment devices which can further restrict heating of the region outside the target region are demanded.

Means for Achieving the Objects

The present invention relates to a handpiece of a laser treatment device. The handpiece includes an optical fiber which guides laser light emitted from a pulse light source; and a revolving holder which holds a tip portion of the optical fiber such that the tip portion is tilted with respect to a rotational axis to direct an optical axis of the laser light towards a target point located on the rotational axis and revolves the tip portion of the optical fiber about the rotational axis. Further, a pulse number of the pulse light source per unit time and a number of revolutions of the tip portion of the optical fiber per unit time are determined such that the pulse number per unit time of the pulse light source is not an integral multiple of the number of revolutions of the tip portion of the optical fiber per unit time.

Further, in the above invention, it is preferable that the revolving holder slidably holds the tip portion of the optical fiber. It is further preferable that a stopper that prevents the tip portion from falling out from the revolving holder is provided at the tip portion of the optical fiber.

Effects of the Invention

The present invention can restrict a temperature rise of tissues in a path from an irradiation unit to a target region as compared with the prior art.

BEST MODE FOR CARRYING OUT THE INVENTION

Figure 1:
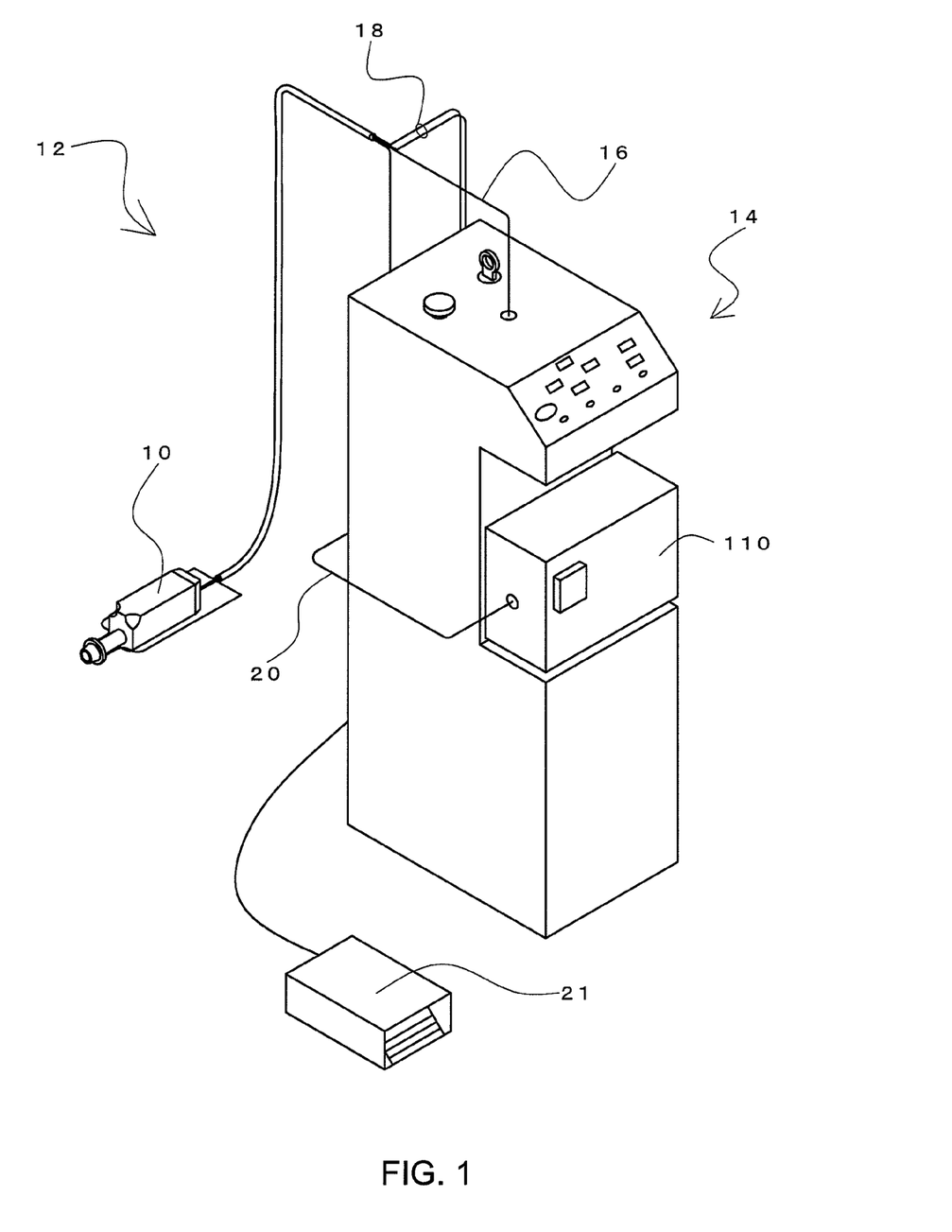
FIG. 1 shows an example of a laser treatment device provided with a handpiece according to a present embodiment.

FIG. 1 shows an example of a laser treatment device 12 including a handpiece 10 according to the present embodiment. The laser treatment device 12 is structured to include the handpiece 10 and a power supply device 14. The power supply device 14 is provided with a laser light source, a power supply, and a coolant circulation pump, all of which are not shown. The handpiece 10 and the power supply device 14 are connected by an optical fiber 16, a coolant circulation tube 18, and an electric power cable 20.

The laser light source of the power supply device 14 is determined in consideration of a treatment target. For example, if the treatment target is tissues under the epidermis such as the dermis, it is preferable to use a laser light source of so-called tissue transmission type. The transmission type laser light has an energy transmittance of 60% or higher at 3 mm from an irradiation source in water. For example, laser light sources such as an Nd:YAG laser, a semiconductor laser, an He—Ne laser, and an argon gas laser are used. Energy density of the laser light source may be at a level having a low risk to the damage treatment region, preferably equal to or less than 23 $J/cm^2$, for example. Furthermore, although the laser light source may be either one of a pulse light source and a continuous light source, a pulse light source which intermittently radiates laser light is preferable, in order to reduce a burden on the skin.

Further, the power supply device 14 is provided with a pedal (foot switch) 21. By stepping on the pedal 21, electric power is supplied to the handpiece 10 from the power supply of the power supply device 14 via the electric power cable 20; and laser light is transmitted from the laser light source to the handpiece 10 via the optical fiber 16.

A controller 110 may be provided between the pedal 21 and the power supply device 14. The controller 110 sends instructions such as energy amount of laser light and irradiation pattern to the power supply device 14 in accordance with the operation of the pedal 21. The controller 110 is provided with a socket to which a connector of the pedal 21 can be inserted and a connector which can be inserted to a socket of the power supply device 14. When the shape of the socket of the power supply device 14 is different depending on the manufacturer of the power supply device 14, a connector which matches the individual socket maybe provided, or an adapter for adapting the connector to the socket may be provided.

Further, the coolant circulation pump and handpiece 10 are arranged so that coolant is circulated via the coolant circulation tube 18. The circulation of the coolant may always be performed regardless of the operation of the pedal, or performed in accordance with the operation of the pedal.

Figure 2:
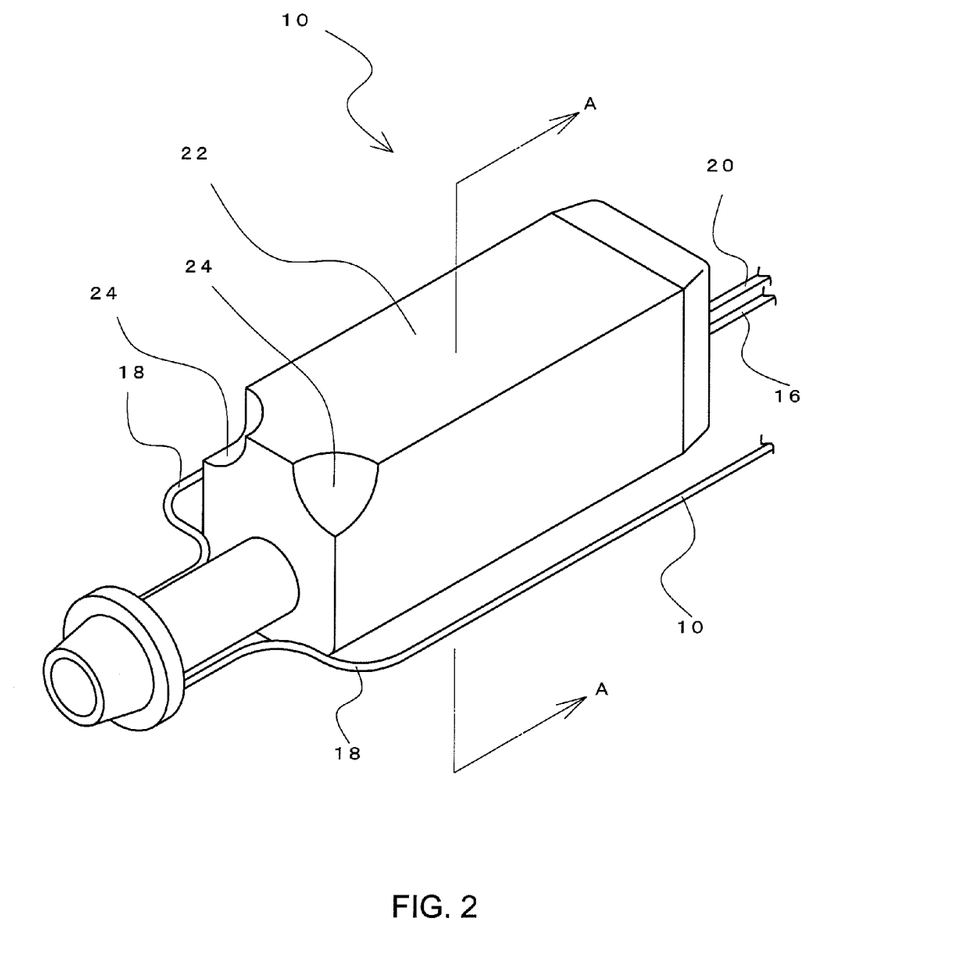
FIG. 2 is a perspective diagram of a handpiece according to the present embodiment.

FIG. 2 shows an enlarged view of the handpiece 10. It is preferable that the handpiece 10 is arranged to have a shape and size such that a practitioner can easily hold it with a hand to operate the handpiece 10. For example, the handpiece 10 may have a pen shape which is 20 to 30 cm long in the longitudinal direction with a holding portion 22 having a shape easily holdable by a practitioner. It is preferable that the holding portion 22 has, for example, a cylindrical or oblique prism shape with chamfered edges. Furthermore, a finger rest 24 on which a practitioner can place his/her finger tips may be provided. The handpiece 10 is formed to weigh, for example, from 0.2 kg to 2 kg such that a practitioner can endure holding the handpiece 10 for a long period of time.

Figure 3:
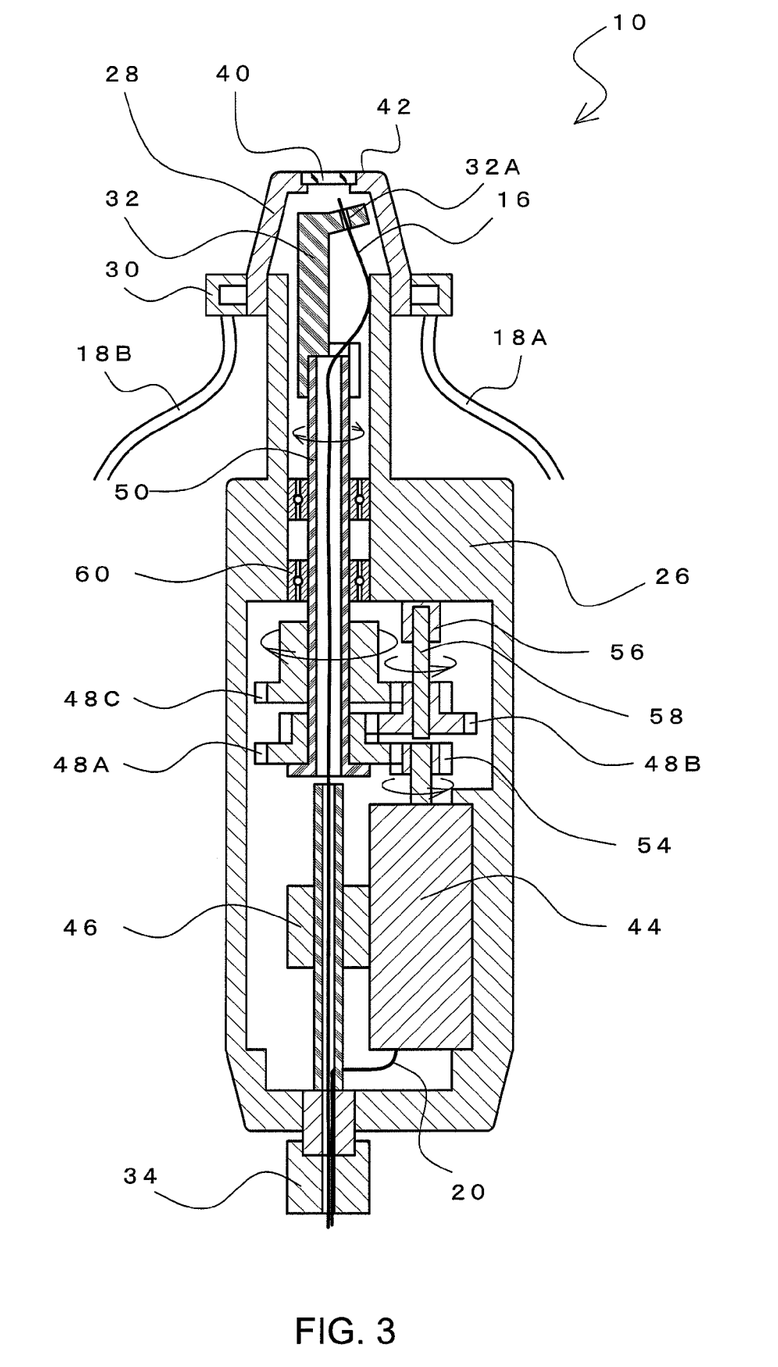
FIG. 3 is a cross-sectional view of the handpiece according to the present embodiment.

FIG. 3 shows a cross-sectional view of the handpiece 10 taken along line A-A in FIG. 2. The handpiece 10 is structured to include the optical fiber 16, the coolant circulation tube 18, the electric power cable 20, a casing 26, a cap 28, a cooling ring 30, a revolving holder 32, a motor 44, a rotation speed sensor 46, a reduction gear 48, and a rotational cylinder 50. The casing 26 is a cylindrical member which forms the holding portion 22 (refer to FIG. 2). The casing 26 houses the revolving holder 32, the motor 44, the reduction gear 48, and the rotational cylinder 50. Further, the casing 26 is structured to receive the optical fiber 16 installed from the outside and to have an irradiation window 40 provided on the cap 28. Laser light can be radiated through the irradiation window 40. Further, the electric power cable 20 is introduced into the casing 26 to supply electric power to the motor 44. The optical fiber 16 and the electric power cable 20 are introduced to the casing 26 from the outside through a connector 34 provided on the rear end of the casing 26.

Although it is possible to form the casing 26 from a metallic material such as aluminum and steel or a resin material such as plastic, it is preferable that the casing 26 be formed from aluminum or plastic having a low specific gravity, in order to reduce the burden imposed on the practitioner.

The cap 28 is mounted on a tip portion (top side on the page) of the casing 26. The cap 28 is a cylindrical member which is tapered such that the tip becomes narrower than the rear end, which has a shape to be fixed onto the tip portion of the casing 26 such as by engagement. The irradiation window 40 is provided on the tip of the cap 28.

The irradiation window 40 is formed from a member through which laser light radiated from the optical fiber 16 can be transmitted. The irradiation window 40 is preferably formed from, for example, sapphire glass. The irradiation window 40 is provided in an area where laser light introduced by the optical fiber revolvable about a rotational axis C0 (refer to FIG. 4) mentioned below is radiated from the tip portion of the casing 26. The irradiation window 40 has, for example, a circular shape having the rotational axis C0 at the center.

Further, the irradiation window 40 and the tip portion of the cap 28 form a contact surface 42 which is to be brought in contact with the skin or the like near the target region to be treated. The cap 28 is mounted on the tip portion of the casing 26 such that when the contact surface 42 is brought in contact with the skin or the like, the contact surface 42 becomes vertical with respect to the rotational axis C0. It should be noted that "vertical" is not limited to exactly 90° only, but a possible error caused from assembly may be allowed in a range from 85° to 95°.

It is preferable that corners of the cap 28 are chamfered to avoid giving a discomfort to a patient caused by the cap 28 being caught by the skin when the contact surface 42 is moved (the contact surface 42 is slid on the skin) while keeping the contact surface 42 in contact with the skin during treatment.

It is further preferable that the cap 28 be formed from a highly heat-conductive material; for example, a metallic material such as aluminum. By the use of the highly heat-conductive material for the cap 28, it becomes possible to rapidly cool the irradiation window 40 heated by laser light and restrict this heat from propagating to the affected area on the skin or the like.

Figure 8:
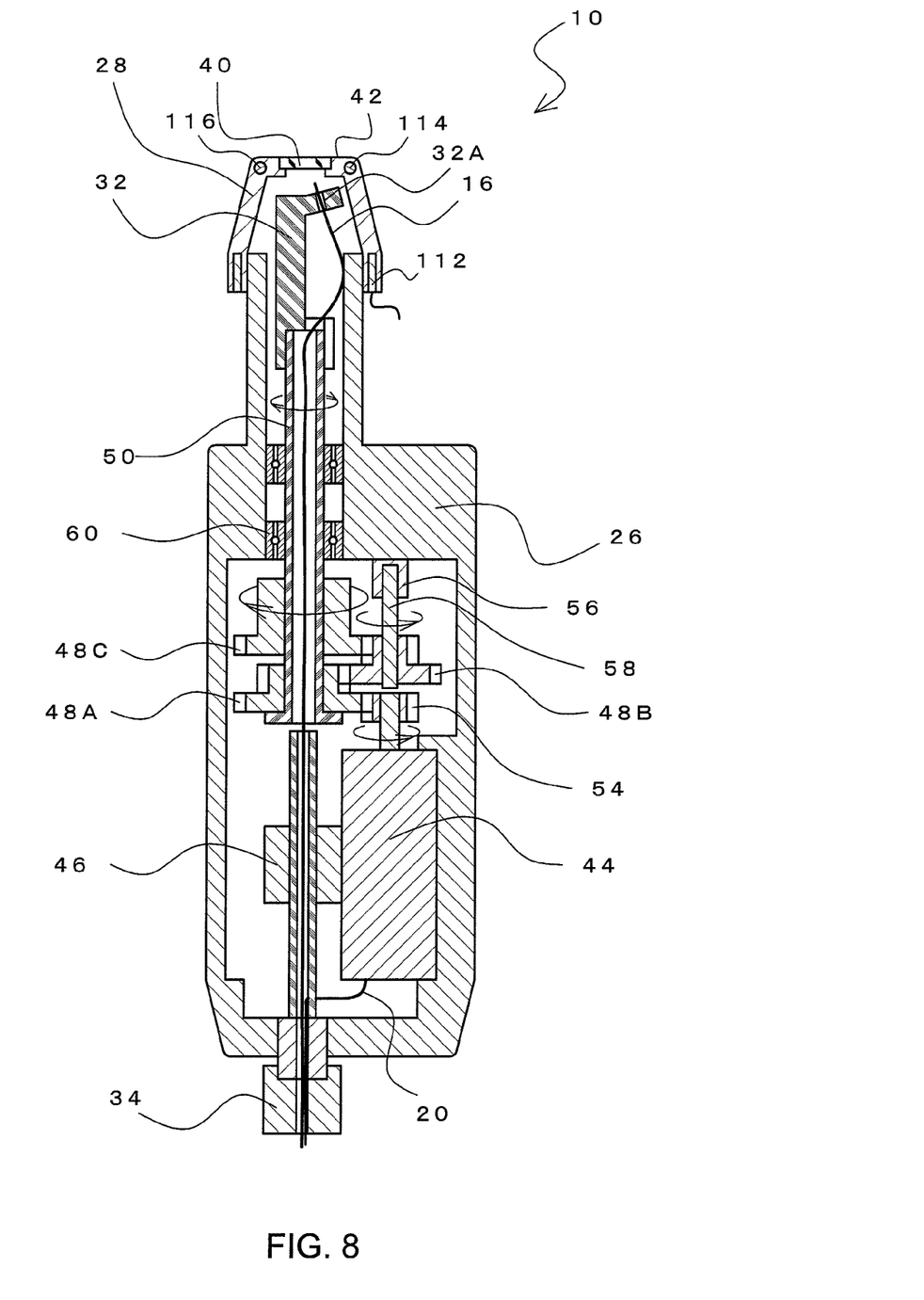
FIG. 8 is a cross-sectional view of the handpiece according to the other embodiment.

Further, the cooling ring 30 may be provided with the cap 28 for cooling the affected area such as the skin heated by laser light . For example, the cooling ring 30 maybe a hollow ring portion arranged around the outer circumference of the cap 28 such that supply and discharge of coolant are enabled through two coolant circulation tubes 18A, 18B connected to the cap 28. In this way, it is possible to efficiently remove heat propagated from the irradiation window 40 via the cap 28, by means of the coolant. It should be noted that the cap 28 can be cooled by air by removing the coolant circulation tubes 18A, 18B removed from the cooling ring 30, or by not providing the cooling ring 30. As shown in FIG. 8, the cap 28 may be provided with an electric cooling unit 112 such as a Peltier device.

Further, the cap 28 may be provided with various other functions. For example, a temperature sensor 114 may be provided. The temperature sensor 114 maybe formed from, for example, a thermo couple. It is preferable to provide the temperature sensor 114 near the irradiation window 40 to facilitate measurement and calculation of the temperature of the target region.

Further, a contact sensor 116 may be provided with the cap 28 in consideration of safety of procedures. For example, radiation of laser light from the handpiece 10 may be prevented even when the pedal 21 is stepped on, if the contact sensor 116 detects no contact with the skin. The contact sensor 116 may be configured from, for example, a capacitance sensor.

Referring back to FIG. 3, the revolving holder 32, the motor 44, the reduction gear 48, and the rotational cylinder 50 for revolving the optical fiber 16 are provided inside the casing 26. As shown in the enlarged cross-sectional view of the tip portion of the handpiece 10 in FIG. 4, the revolving holder 32 holds the tip portion 64 of the optical fiber 16 such that the tip portion of the optical fiber 16 circles about the rotational axis C0 by revolving the revolving holder 32 by the motor 44 via the reduction gear 48 and rotational cylinder 50.

In the present embodiment, the rotation of the motor 44 is transmitted to the revolving holder 32 via the reduction gear 48. Specifically, the rotation of the motor 44 is transmitted from an output gear 54 of the motor 44 to a first reduction gear 48A. The first reduction gear 48A is slidably held such that the first reduction gear 48A can be rotated around the rotational cylinder 50 while sliding. Further, the first reduction gear 48A is engaged with a second reduction gear 48B fixed on a shaft 58 which is rotationally held by a bearing 56. The rotation of the first reduction gear 48A is reduced and transmitted to the second reduction gear 48B in accordance with a gear ratio between the first reduction gear 48A and the second reduction gear 48B. The second reduction gear 48B is further engaged with a third reduction gear 48C fixed to the rotational cylinder 50. The rotation of the second reduction gear 48B is reduced and transmitted to the third reduction gear 48C in accordance with a gear ratio between the second reduction gear 48B and the third reduction gear 48C. In this way, the rotational cylinder 50 rotates together with the rotation of the third reduction gear 48C. The rotational cylinder 50 is rotatably held by a bearing 60 on an internal wall of the casing 26 and fixes the revolving holder 32.

It should be noted that the reduction gear 48 can be omitted if the control range of rotation rate of the motor 44 is within a desired rotation rate of the optical fiber 16.

Further, the rotation speed and number of rotations per unit time of the motor 44 are sensed by the rotation speed sensor 46 and sent to the power supply device 14. A controller of the power supply device 14 calculates the rotation speed and the number of revolutions per unit time of the optical fiber 16 based on the rotation speed of the motor 44 sensed by the rotation speed sensor 46 and previously stored reduction ratios of the reduction gears 48A to 48C.

Figure 4:
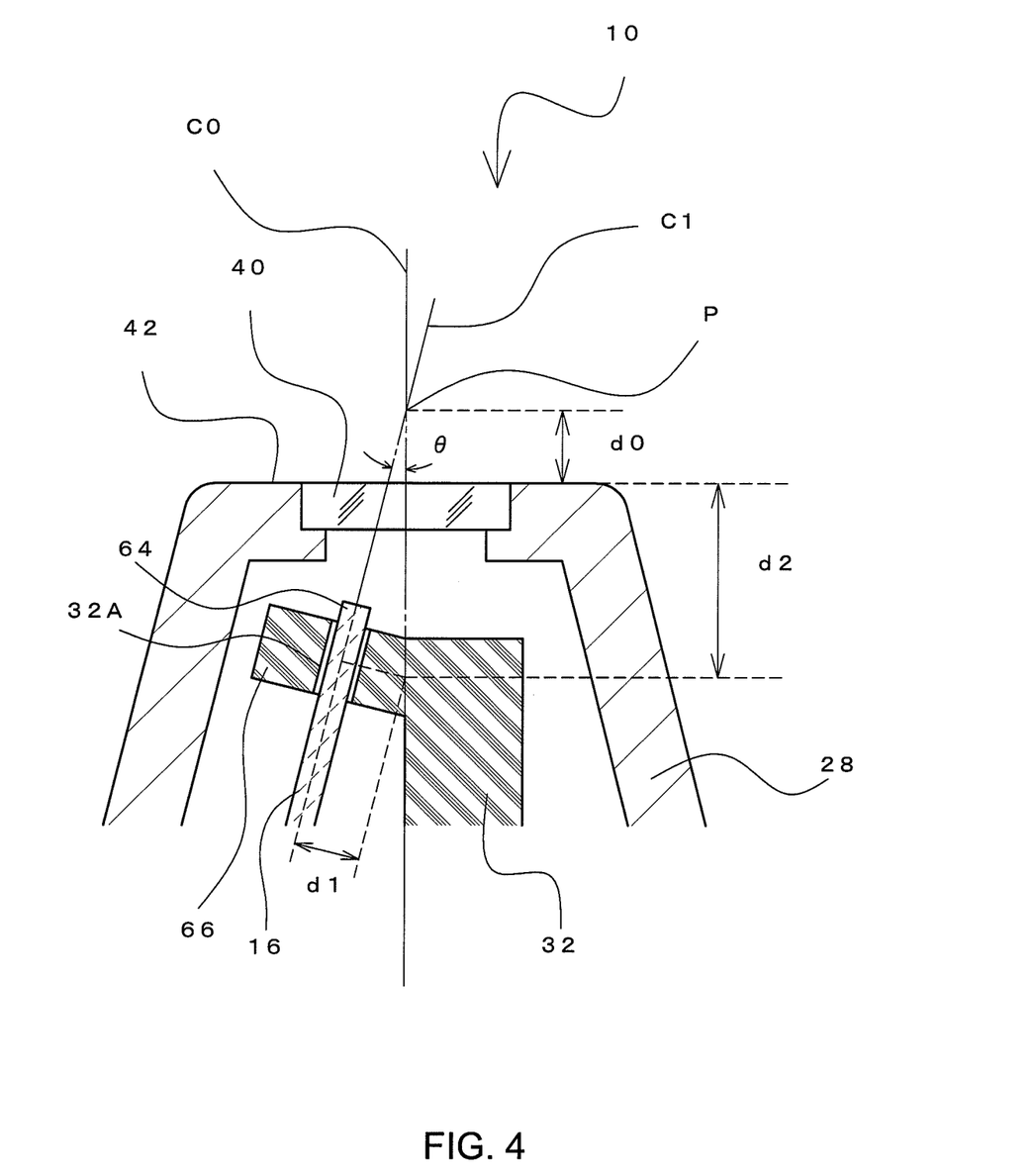
FIG. 4 is an enlarged cross-sectional view of a tip portion of the handpiece according to the present embodiment.

The optical fiber 16 passes through the rotational cylinder 50 having a hollow cylindrical shape and is slidably held by the revolving holder 32. A structure may be arranged such that, for example, as shown in FIG. 4, the optical fiber 16 is held by insertion through an insertion hole 32A provided with the revolving holder 32. By making the internal diameter of the insertion hole 32A slightly larger than the outer diameter of the optical fiber 16, the optical fiber 16 can be slidably held by the revolving holder 32. In this way, when the revolving holder 32 is revolved along with the rotation of the rotational cylinder 50, the optical fiber 16 is revolved along with the revolving holder 32, while sliding at the holding portion of the revolving holder 32, and thus, it is possible to avoid twisting of the optical fiber 16. Further, although in FIG. 4 the optical fiber 16 is held with the tip portion 64 protruding from the insertion hole 32A of the revolving holder 32, the optical fiber 16 may be held such that the tip portion 64 is encased within the insertion hole 32A of the revolving holder 32.

Further, in the present embodiment, the optical fiber 16 is held at a position deviated from the rotational axis C0 of the revolving holder 32 such that the optical axis C1 of the optical fiber 16 is tilted with regard to the rotational axis C1. The tilt angle θ of the optical fiber 16 with respect to the rotational axis C0 is set such that the rotational axis C0 and the optical axis C1 are crossed at a target point P. The target point P is determined based on a distance d0 between the contact surface 42 and a target region with the contact surface 42 of the casing 26 in contact with the affected area (the skin) such that the target region to be warmed is located on the rotational axis C1. For example, when the target region is in the dermis, it is preferable that the distance d0 is from 0.5 mm to 1.0 mm.

Specifically, as shown in FIG. 4, a tilt angle θ can be determined by an equation, tilt angle $\theta = \tan^{-1}(d1/(d0+d2))$, where d1 represents a length of a perpendicular line which is drawn down from the center point in the width direction of a holding portion 66 of the revolving holder 32; and d2 represents a distance between the intersection point of the perpendicular line and the rotational axis C0, and the contact surface 42.

The tilt angle θ of the optical axis C1 with regard to the rotational axis C0 is set in a range of 0°<θ<90°. However, because an excessively small tilt angle θ causes areas outside the target region to be overly heated because of the concentrated radiation of laser light to the area, it is preferable that the tilt angle θ be set to be wider than the angle which heats an area outside the target region above a desired temperature. On the other hand, because an excessively large tilt angle θ causes the revolution diameter of the optical fiber 16 to become large, and thus the diameter of the handpiece 10 is enlarged resulting in a risk of reduced usability, it is preferable that the tilt angle θ be less than the angle which satisfies a desired level of usability.

Generally, as d1 is set from 3.0 mm to 5.0 mm and d2 is set from 5 mm to 10 mm, when d0 is from 0.5 mm to 1.0 mm, the tilt angle θ is within a range from 15° to 45°.

Figure 9:
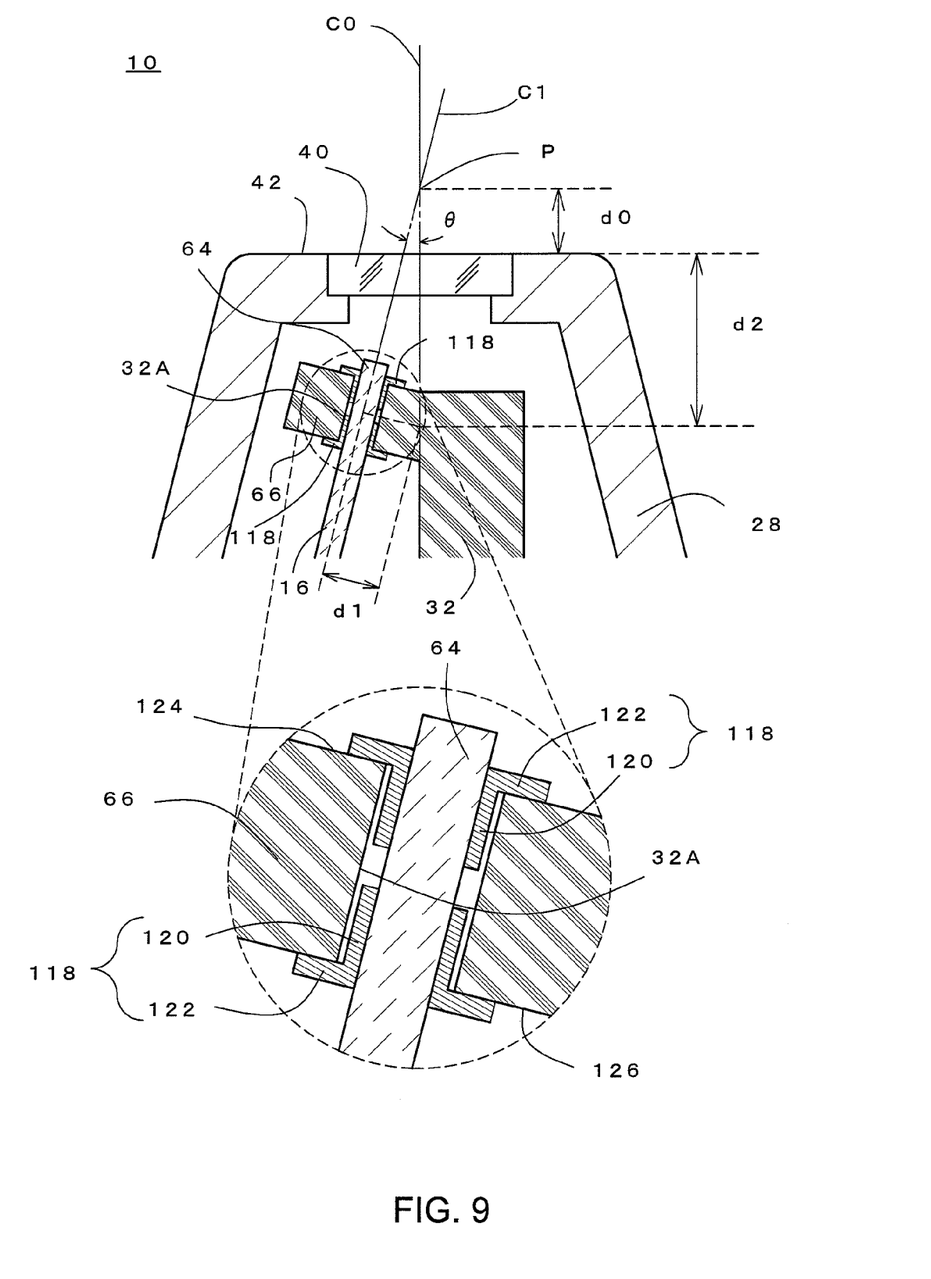
FIG. 9 is an enlarged cross-sectional view of a tip portion of the handpiece according to the other embodiment.

It should be noted that there is a risk that the tip portion 64 of the optical fiber 16 falls out from the revolving holder 32 due to centrifugal force and deflection or the like during the revolution of the optical fiber 16 while sliding with respect to the revolving holder 32. Thus, as shown in FIG. 9, a stopper 118 may be provided at the tip portion 64.

The stopper 118 is formed to include a cylindrical portion 120 and a flange portion 122. The cylindrical portion 120 is inserted and fixed to the tip portion 64 and is slidable with respect to the revolving holder 32. The cylindrical portion 120 may be formed to have, for example, a cylindrical shape with an outer diameter smaller than the inner diameter of the optical fiber insertion hole 32A of the revolving holder 32 and an internal diameter larger than the outer diameter of the tip portion 64. Further, the flange portion 122 is a flat panel member with a diameter larger than the optical fiber insertion hole 32A of the revolving holder 32. Similar to the cylindrical portion 120, the flange portion 122 is slidable with respect to the revolving holder 32. For example, the cylindrical portion 120 and the flange portion 122 maybe formed from resin such as Teflon® which provides good slidability.

The stopper 118 is fixed to the tip portion 64 such that the flange portion 122 touches a side surface 124 of the holding portion 66 on the irradiation window 40 side. For example, the stopper 118 may be fixed by adhesion to the tip portion 64, or the stopper 118 may be fixed to the tip portion 64 by mechanical fastening.

Further, the stopper 118 may be provided also on the holding portion 66 on a side surface 126 side on the opposite side of the side surface 124. By providing the stopper 118 on the side surface 126 side, it becomes possible to prevent the tip portion 64 from protruding on the irradiation window 40 side.

Referring back to FIG. 4, treatment using the handpiece 10 for a laser treatment device according to the present embodiment is described. As an example, described below is a case where the target region is dermis tissues immediately below a wrinkle formed in the skin.

It is known that collagen fibers increase by warming dermis tissues. It is also known that increase of collagen fibers reduces wrinkles and sagging of skin or the like. The inventors found that collagen fibers significantly increase by warming a dermis layer from 1 mm to 3 mm immediately below the skin to a range from 46° C. to 68° C. By assuming a certain point in the dermis layer as a target region, when the output of laser light is 9 W, the target region can be warmed to the above temperature range by continuously radiating laser light to the target region for six seconds or longer. On the other hand, when the laser irradiation is continued on the target region for a long period of time, a patient will be unable to endure the pain of the target region. Therefore, the irradiation time to a target region is preferably 10 seconds or less.

It should be noted that, as described above, it is necessary to accurately perform the temperature control of the target region and its periphery during treatment. Thus, prior to treatment, preprocessing may be performed to adjust the temperature of the skin to a predetermined temperature in advance. For example, prior to radiation of laser light, a cooling process may be performed to cool the skin down to a range from 5° C. to 20° C. Further, the cooling of the skin may be stopped during radiation of laser light in order to accurately control the temperature of the target region.

In radiating laser light, the contact surface 42 of the handpiece 10 is brought in contact with the skin surface such that the rotational axis C0 is directed towards the target region to be treated. On this occasion, by bringing the contact surface 42 in contact with a wrinkle, the target region immediately below the wrinkle and a target point P can be overlapped, because the contact surface 42 of the handpiece 10 is formed to be perpendicular with respect to the rotational axis C0 and the target point P is set on the rotational axis C0.

Further, by stepping on the pedal 21, electric power is supplied to the motor 44 and laser light is transmitted to the optical fiber. The optical fiber 16 radiates laser light towards the target point P while revolving about the rotational axis C0 along with the rotation of the motor 44.

Figure 5:
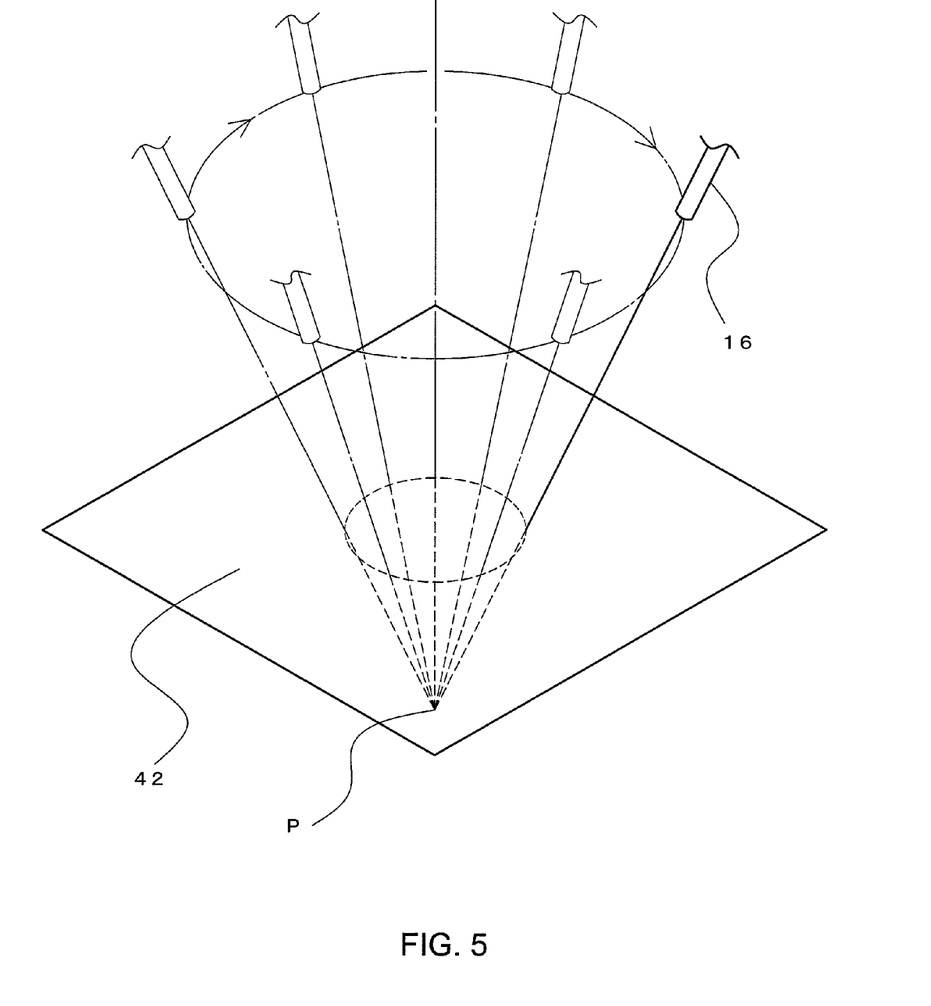
FIG. 5 is a diagram to illustrate treatment by using the handpiece according to the present embodiment.

On this occasion, as shown in FIG. 5, the target region which is overlapped with the target point P is continuously irradiated with laser light. On the other hand, the area outside the target region is intermittently irradiated with laser light. In other words, the laser light irradiation time in the area outside the target region is shorter than that in the target region. Therefore, the temperature rise in the area outside the target region is slower than that in the target region. As a result, while the target region is intensively warmed, the temperature rise of the tissues in the path from the optical fiber 16 to the target region can be restricted.

When a laser light source is a pulse light source, it is preferable that the revolution cycle of the optical fiber 16 be set in association with pulse cycle or that the pulse cycle be set in association with the revolution cycle. In other words, the pulse cycle and revolution cycle are shifted from each other such that a certain point in the area outside the target region is not intensively irradiated with laser light and the laser light is radiated evenly (not concentrated on a certain region) to the area outside the target region. For example, it is preferable that the revolution speed and pulse cycle be set to achieve $60 \times 10^3 / A \ne kB$ where "A" represents a pulse cycle A (msec); "B" represents a revolution speed (rpm) of the optical fiber 16; and "k" represent an integer. In this way, it is possible to allow a longer time interval between radiations of laser light to the area outside the target region. A longer time interval makes a heat dissipation period (cool down period) longer. In this way, it becomes possible to restrict the temperature rise of the area outside the target region such as the epidermis.

Figure 6:
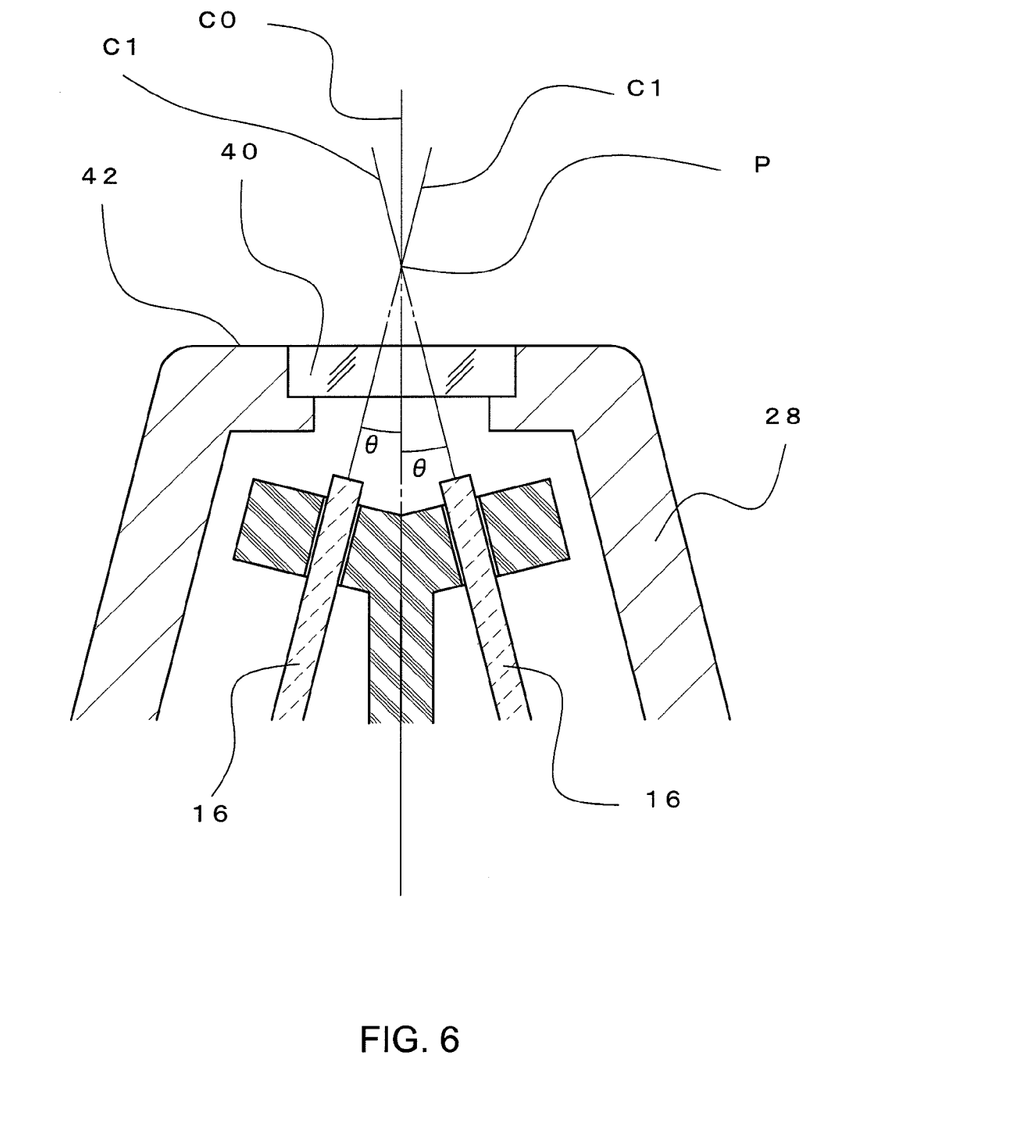
FIG. 6 is an exemplary diagram to show a handpiece of a laser treatment device according to another embodiment.
Figure 7:
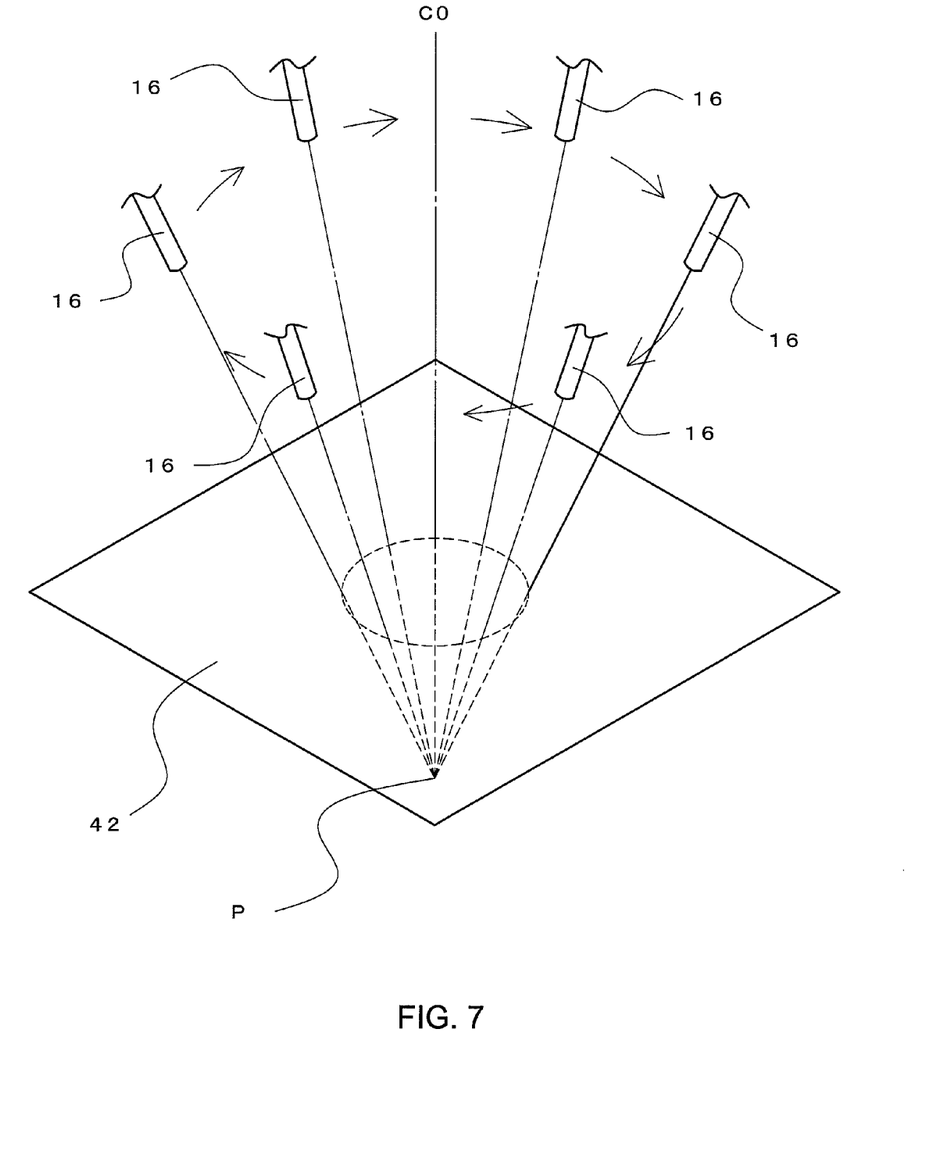
FIG. 7 is a diagram to illustrate treatment by using the handpiece according to the other embodiment.

It should be noted that, although one piece of optical fiber 16 is used in the above embodiment, two or more pieces of optical fiber 16 may be used. Further, when two or more pieces of optical fiber 16 are used, these optical fibers 16 may or may not be revolved. For example, in the latter case, as shown in FIG. 6, two or more pieces of optical fibers 16 are arranged around the central axis C0. On this occasion, a holding portion 66 holds each optical fiber 16 in a manner that each optical fiber 16 tilts with respect to the central axis C0 such that all of the optical axes C1 of the respective optical fibers 16 are crossed at a target point P. The tilt angle θ is preferably from 15° to 45°. Further, during treatment, each optical fiber 16 sequentially radiates laser light as shown in FIG. 7. Although, in FIG. 7, the irradiation order of each optical fiber 16 is determined such that the laser is radiated to the target point P while drawing a circle, the irradiation order can be determined regardless of this embodiment so long as the irradiation frequency of each optical fiber 16 is uniform. The irradiation order from each optical fiber 16 is controlled by a light guide switch unit (not shown) provided with the power supply device 14. Also in this embodiment, the target point P is intensively irradiated with laser light, while the other areas are intermittently irradiated, and thus the temperature rise of the tissues in the path from the optical fiber 16 to the target point P can be restricted.

REFERENCE NUMERALS 10 handpiece, 12 laser treatment device, 14 power supply device, 16 optical fiber, 18 coolant circulation tube, 20 electric power cable, 21 pedal, 22 holding portion of casing, 24 finger rest, 26 casing, 28 cap, 30 cooling ring, 32 revolving holder, 32A optical fiber insertion hole, 34 connector, 40 irradiation window, 42 cap contact surface, 44 motor, 46 rotation speed sensor, 48 reduction gear, 50 rotational cylinder, 54 output gear, 56 shaft bearing, 58 shaft, 60 rotational cylinder bearing, 64 tip portion of optical fiber, 66 holding portion, 110 controller, 112 cooling unit, 114 temperature sensor, 116 contact sensor, 118 stopper, 120 cylindrical portion, 122 flange portion.

The invention claimed is:

1. A handpiece of a laser treatment device, comprising:
an optical fiber which is configured to guide laser light emitted from a pulse light source; and
a revolving holder which is configured to hold a tip portion of the optical fiber such that the tip portion is tilted with respect to a rotational axis to direct an optical axis of the laser light towards a target point located on the rotational axis, the revolving holder revolving the tip portion of the optical fiber about the rotational axis,
wherein an irradiation pattern of the pulse light source is adjusted by a control unit;
the revolving holder is controlled by the control unit so that a number of revolutions of the tip portion of the optical fiber per unit time is adjusted; and
the control unit is configured to determine a pulse number of the pulse light source per unit time and the number of revolutions of the tip portion of the optical fiber per unit time such that the pulse number of the pulse light source per unit time is not an integral multiple of the number of revolutions of the tip portion of the optical fiber per unit time.

2. The handpiece of the laser treatment device according to claim 1, wherein the revolving holder slidably holds the tip portion of the optical fiber, and a stopper preventing the tip portion from falling out from the revolving holder is provided at the tip portion of the optical fiber.

* * * * *